United States Patent [19]

Fujimura et al.

[11] Patent Number: 4,880,744

[45] Date of Patent: Nov. 14, 1989

[54] METHOD OF CULTURING PROTOPLASTS

[75] Inventors: Tatsuhito Fujimura, Tokyo; Motoi Sakurai, Kanagawa, Japan

[73] Assignee: Mitsui Toatsu Chemicals, Inc., Tokyo, Japan

[21] Appl. No.: 865,423

[22] Filed: May 21, 1986

[30] Foreign Application Priority Data

May 21, 1985 [JP] Japan ................... 60-106886

[51] Int. Cl.$^4$ ............................................. C12N 5/02
[52] U.S. Cl. ........................ 435/240.46; 435/240.45; 435/240.47; 435/240.5; 435/240.54
[58] Field of Search ............ 47/58; 435/240.5, 240.54, 435/240.49, 172.2, 240.47, 240.46, 240.45

[56] References Cited

FOREIGN PATENT DOCUMENTS 0009319 4/1980 European Pat. Off. .
0125159 11/1984 European Pat. Off. .
0202667 11/1986 European Pat. Off. .
0202668 11/1986 European Pat. Off. .

OTHER PUBLICATIONS

Aviv et al., (1984), in Cell Culture & Somatic Cell Genetics of Plants, vol. 1.
Wakasa et al., (1984), J. Plant Physical, 117:223-31.
Xu et al., (1981), J. Expt. Botany, 32:767-778.
K. W. Hughes, (1981), in B. V. Conger, Ed., Cloning Agricultural Plants . . . , CRC Press, Inc., Boca Raton, Fla., pp. 21-22.
Flores et al., (1981), in Advances in Cell Culture, vol. 1, Academic Press, Inc., N.Y., p. 249.
Evans et al., (1983), in Int. Rev. of Cytol., Suppl. 16, K. L. Giles, Ed., Academic Press, N.Y., pp. 43 and 49.
Fitter et al., (1983), Plant Protoplasts, Publication of Hoechst Corporation.
Gamborg, Cell Culture and Somatic Cell Genetic of Plants, vol. 1, pp. 18-26, (1984).
Biological Abstracts, vol. 68, No. 11595, (1979).
Fujimura et al., Plant Tissue Culture Letters, vol. 2, No. 2, pp. 74-75, (1985).
Molec. Gen. Genet., vol. 145, pp. 239-243, (1976), Deka et al.
Wakasa et al., J. Plant Physiol., vol. 117, pp. 223-231, (1984).
Berlin et al., Adv. I. Biochem., vol. 31, pp. 99-132, (1985).
Chin et al., Ann. Bot., 43, pp. 23-32, (1979).
Ohno et al., Japanese Journal of Breeding, 35, pp. 54-55, (1985).
Nishi et al., Nature, 219, pp. 508-509, (1968).
Gamborg, Cell Culture and Somatic Cell Genetics of Plants, vol. 1, pp. 18-26, (1984).

Primary Examiner—Charles F. Warren
Assistant Examiner—Charles E. Cohen
Attorney, Agent, or Firm—Birch, Stewart, Kolasch & Birch

[57] ABSTRACT

Disclosed is a method of culturing protoplasts in a liquid medium. According to the method of the present invention, the pH of the liquid medium for culturing the protoplasts is adjusted to not more than 5.2.

22 Claims, No Drawings

METHOD OF CULTURING PROTOPLASTS

BACKGROUND OF THE INVENTION

I. Field of the Invention

This invention relates to a method of culturing a protoplast. More specifically, this invention relates to a method of culturing a protoplast in a liquid medium, by which a cell cluster or a callus is derived from the protoplast.

II. Description of the Prior Art

A protoplast is a cell of a plant, bacterium, fungus or the like from which the cell wall has been removed. Since the protoplast does not have a cell wall, it is easily subjected to an artificial manipulation such as cell fusion, gene manipulation and artificial somatic cell mutation. Thus, if a complete plant can be regenerated from a manipulated protoplast it would be possible to obtain a plant which has an advantageous characteristic which the wild type plant does not have. It is known for many plants that a complete plant can be regenerated from a callus or a cell cluster. Thus, if a callus can be derived from a protoplast, a complete plant is likely to be regenerated from the callus, and in turn, from the protoplast.

Some techniques are known for dicotyledons such as tobacco by which a complete plant can be regenerated from a protoplast. However, as for the gramineous plants such as rice, wheat and corn, complete plants were reported to be regenerated only for corn and pasture. As to rice, very few techniques have been reported as mentioned below. The conventional culturing methods of the protoplasts include culturing the protoplasts by embedding the protoplast in a semi-solid agar medium, by suspending the protoplast in a liquid medium, and by culturing the protoplast using feeder cells. However, it has been found that these techniques are often not effective for culturing other plants such as gramineous plants including rice, wheat and corn. For example, if a protoplast of rice is cultured by one of these methods, the protoplast dies or cannot grow.

As for culturing techniques of the protoplast of rice, it has been reported that a callus was derived from a protoplast obtained from a cell lacking its nitrate reductase (Wakasa et al., J. Plant Physiol. 117: pp. 223-231, (1984)), and that a shoot was generated from a callus derived from a protoplast obtained from a callus of a pollen (Ohno et al., Japanese Journal of Breeding 35: pp.54-55, (1985)). However, these techniques utilize protoplasts released from specific calli, and the techniques are applicable to not all kinds of protoplasts released from various kinds of calli or tissues. In other words, these techniques are not reproducible for most kinds of protoplasts.

On the other hand, it has been reported by many researchers that complete plants were regenerated from cultured cells of rice (Nishi et al., Nature 219: pp. 508-509, (1968)). However, these techniques do not utilize the protoplast. Further, it has been found that obtaining a protoplast from cells having a high differentiation ability used in these techniques is difficult, and to culture the protoplast is also difficult.

Thus, a method of culturing protoplasts is needed to be established by which a callus or a cell cluster is derived from the protoplast, which method is reproducible and applicable to protoplasts originated from a general or a non-specific cell of a plant.

SUMMARY OF THE INVENTION

Accordingly, an object of the present invention is to provide a method of culturing a protoplast by which a cell cluster or a callus is derived from the protoplast, which method is reproducible and applicable to protoplasts originated from a general or a non-specific cell of a plant.

According to the method of the present invention, protoplasts are cultured in a liquid medium of which the pH is not more than 5.2. In the conventional methods of culturing protoplasts, the pH of the culture medium was adjusted to 5.5 to 6.0. This invention is based on the surprising discovery made by the present inventors that if the pH of the culture medium is adjusted to 5.2 or less, the protoplasts grow well and form cell clusters.

By the method of the present invention, not only the protoplasts of dicotyledons, but also even the protoplasts of monocotyledons can be grown well to form calli or cell clusters.

DETAILED DESCRIPTION OF THE PREFERRED EMBODIMENTS

As mentioned above, in the method of the present invention, the protoplast is cultured in a liquid medium of which pH is not more than 5.2. Preferred pH of the liquid culture medium is 3.5 to 5.2, and more preferably 4.0 to 4.7. Adjustment of the pH may be accomplished by adding an acid (or a base, in some cases). Any acid (or base) may be used for the adjustment of the pH, as long as it does not adversely affect the growth of the protoplast, and HCl and KOH may be conveniently used for this purpose.

Any medium conventionally used for culturing protoplasts may be used in the method of the present invention after adjusting the pH to 5.2 or less. For example, if the protoplast to be cultured is a protoplast of rice (plants belonging to genus Oryza such as *Oryza sativa*, *Oryza glaberrima* and *Oryza perennis* and so on), MS medium (Murashige and Skoog, Physiol. Plant. 15, pp. 473-479, (1962)), B5 medium (Gamborg et al., Exp. Cell Res. 50, pp. 151-158, (1968)), N6 medium (Chu et al., Scientia Scinica 18, pp. 659-663, (1975)) and R2 medium (Ohira et al., Plant Cell Physiol., 14, pp. 1113-1121, (1973)) may be used as the culture medium. Similarly, if the protoplast to be cultured is a protoplast of petunia, NT medium (Magata and Takebe, Planta 99, pp. 12-20, (1971)) may be used. The medium may contain phytohormones such as 2,4-dichlorophenoxy acetic acid (hereinafter referred to as 2,4-D), indole acetic acid, naphthalene acetic acid, benzyladenine, kinetin, zeatin, gibberellin, and absisic acid; vitamins such as nicotinic acid, thiamine and pyridoxine; sugars and sugar alcohols such as sucrose and mannitol; and other nutrients, which are conventionally added to the culture media for culturing protoplasts. The concentration of these additives may be suitably selected depending on the nature of the protoplast to be cultured, and may be, for example, 0.1 to 100 mg/l for those other than sugars and sugar alcohols, and may be 1 to 30% by weight for sugars and sugar alcohols.

It has been found by the present inventors that if the medium is a conditioned medium, the growth of the protoplast is further promoted. "Conditioned medium" herein used means a medium in which a plant cell or a protoplast was cultured before (hereinafter referred to as "used medium"), as well as the mixture of such used medium and a fresh medium. It is preferred that the conditioned medium contains at least 25% by weight of used medium, and more preferably at least 80% by weight of used medium. It is also preferred that the used medium have been used for culturing the cells of the same species as the protoplast to be cultured, although those used media used for culturing different species of plants may also be used.

The culturing conditions per se may be conventional. Thus, the culturing conditions may be appropriately selected depending on the nature of the protoplast to be cultured. For example, if the protoplast to be cultured is a protoplast of rice, the culturing temperature may be 20° to 30° C., and preferably about 26° C., and the population density of the protoplasts in the liquid medium may be $10^4$ to $10^7$/ml, and preferably $10^5$ to $5 \times 10^6$/ml. Further, it has been found that better results may be obtained by culturing the protoplast in a liquid medium of 100 to 400 μm, especially 200 to 300 μm thickness.

The method of the present invention may be applied to the culture of protoplasts prepared by any method. A number of methods to release protoplasts are known for various kinds of plants. If the protoplast to be cultured is a protoplast of rice, the protoplast may be, for example, obtained from a callus of rice by treating the callus with an enzymatic solution containing 0.1 to 10% by weight, preferably 1 to 5% by weight of cellulase, 0.1 to 5% by weight, preferably 0.5 to 2% by weight of a macerating enzyme, 0 to 5% by weight, preferably 0.1 to 1% by weight of calcium chloride, and 0 to 5% by weight, preferably 0.1 to 1% by weight of potassium salt of dextran sulfate.

This invention will be more readily understood by referring to the following examples. It should be noted that the following examples are presented for illustration purposes only, and the scope of the invention is by no means limited thereto.

Preparation of Protoplasts

Seeds of rice (*Oryza sativa cultivar*, variety: Nihonbare) were immersed in 70% aqueous solution of ethanol for one minute, and then immersed in an aqueous solution of sodium hypochlorite (chlorine content of 5% by weight) for 15 minutes. The seeds were then washed with sterilized distilled water three times and then sowed on N6 agar medium containing 0.3% by weight of casein hydrolysate, 2 ppm of 2,4-D and 1ppm of benzyl adenine. After culturing at 26° C. for three weeks, calli were formed from the scutella of the seeds. These calli were subcultured once every four weeks in the same conditions.

The thus obtained calli were suspended in R2 liquid medium containing 0.3% by weight of casein hydrolysate and 1ppm of 2,4-D. The cells were subcultured once a week. The cell clusters obtained at 5 to 7 days after subculture were used for preparing protoplasts in the next step.

The thus obtained cell clusters were treated with a solution containing 4.0% by weight of Cellulase Onozuka RS (commercially available from Yakult Pharmaceutical), 1.0% by weight of Macerozyme R-10 (commercially available from Yakult Pharmaceutical), 0.5% by weight of calcium chloride, 0.5% by weight of potassium salt of dextran sulfate, and 0.4M of mannitol as an osmoticum. The cells were then gently shaken in this solution for 6 hours at 27° C. to obtain protoplasts. Then the enzymatic solution containing the protoplasts was filtered to remove the undigested cell clusters, and the filtrate was centrifuged at 50g for 5 minutes to precipitate the protoplasts. The precipitated protoplasts were washed three times with 0.4M aqueous solution of glucose and were cultured in the next step.

CULTURE OF PROTOPLASTS (EXAMPLE 1)

R2 media containing 1 ppm of 2,4-D and 0.4 M of sucrose, and having different pH as shown in the Table were used for culturing the protoplasts obtained in the above-described step. Two hundred microliters of each of the media was placed in a plastic Petri dish of 35 mm diameter, of which bottom surface was coated with a thin agar layer, and 30 μl of a suspension of the protoplasts containing $10^6$ protoplasts/ml was added thereto, and the suspension was spread uniformly. After sealing the Petri dishes, culture was conducted in the dark at 26° C. for 30 days. The formation of cell clusters was observed using an inverted microscope. The results are shown in the Table.

CULTURE OF PROTOPLAST (EXAMPLE 2)

Protoplasts were prepared in the same manner as described above from scutella of rice (*Oryza sativa cultivar*, variety: Nihonbare). The R2-based medium used in the above step for culturing the calli of rice was filtered to obtain a filtrate (used medium). To 10 ml of this filtrate, were added 50 μl of 2,4-D of a concentration of 100 ppm and 1.37 g of sucrose. A fresh R2 medium was supplemented to this used medium at a ratio o 4:1 (W/W) (used medium 4:fresh medium 1) to obtain a conditioned medium. This medium was then filtered through 10 a membrane filter to sterilize the same.

The thus obtained conditioned medium was divided in portions and the pH of each of them was adjusted to a value shown in the Table with 0.1 N HCl. The protoplasts were cultured in each conditioned medium in the same manner as in Example 1. The formation of cell clusters was observed with an inverted microscope. The results are shown in the Table.

TABLE

| | Formation of Small Cell Clusters | | |
|---|---|---|---|
| | Medium pH | Example 1 | Example 2 |
| Outside the Invention | 6.0 | — | — |
| | 5.5 | — | — |
| | 5.2 | ± | + |
| | 5.0 | ± | + |
| The Invention | 4.7 | ± | + + |
| | 4.5 | ± | + + |
| | 4.3 | ± | + + |
| | 4.0 | ± | + + |
| | 3.5 | ± | + |

−No cell clusters were formed
±Several cell clusters were formed
+Several tens of cell clusters were formed
+ +Several hundred of cell clusters were formed As shown in the Table, by using a medium of which pH is 3.5 to 5.2, cell clusters were formed from the protoplasts, while by using a medium of which pH is 5.5 or 6.0, no cell clusters were formed. It can also be seen that pH of 4.0 to 4.7 is especially preferred. Further, it can be seen that by using conditioned medium, better results are obtained than those obtained by using fresh medium.

CULTURE OF PROTOPLASTA (EXAMPLE 3)

The same procedure as in Example 2 was repeated except that the ratio (W/W) of used medium to fresh medium was 1:4. The same results as in Example 1 were obtained. Thus, it can be seen that by using a conditioned medium containing 80% by weight of used medium (Example 2), better results are obtained than those obtained by using a conditioned medium containing 20% by weight of used medium (Example 3).

We claim:

1. A method of culturing protoplasts comprising: culturing protoplasts of rice at a cell density sufficient to allow growth of said protoplasts in a liquid medium having a pH effective for culturing said protoplasts which is 3.5 to 5.2 and on a hydrophilic support on which said liquid medium can spread uniformly.

2. The method of claim 1 wherein the pH of the medium is 4.0 to 4.7.

3. The method of claims 1 or 3 wherein the medium is a conditioned medium which comprises at least 25% by weight of a medium which has been used for culturing a cell.

4. The method of claims 1 or 3 wherein the conditioned medium comprises at least 80% by weight of a used medium.

5. The method of claim 3 wherein the cell cultured in the used medium contained in the conditioned medium is of the same species as the protoplast to be cultured in the conditioned medium.

6. The method of claim 3 wherein the rice is Oryza sativa.

7. The method of claim 1 wherein the rice is Oryza sativa.

8. The method of claim 1 wherein the medium comprises as its basal medium R2, N6, B5 or MS medium.

9. The method of claim 6 wherein the medium further comprises 0.1 to 10 mg/1 of 2,4-D.

10. The method of claim 1, wherein the pH of the medium is 5.2.

11. The method of claim 1, wherein the pH of the medium is about 5.0.

12. The method of claim 1, wherein said protoplast is a protoplast of *Oryza perennis*.

13. The method of claim 1, wherein said protoplast is a protoplast of *Oryza glaberrima*.

14. The method of claim 1, wherein said protoplast is a protoplast of *Oryza sativa*, variety Nihonbare.

15. The method of claim 1, wherein said hydrophilic support is a thin agar layer.

16. The method of claim 1, wherein said hydrophilic support is a support which absorbs water.

17. The method of claim 1, wherein a thin layer of said hydrophilic support is disposed on a surface of a container which is sealed during culturing.

18. The method of claim 17, wherein said container is a petri dish.

19. The method of claim 18, wherein said hydrophilic support is agar.

20. A method of culturing protoplasts of rice, comprising the steps of:
culturing protoplasts from scutella of *Oryza sativa*, variety, Nihonbare at a cell density sufficient to allow growth of said protoplasts in a conditioned R2 medium containing 0.1 to 10mg/l 2, 4-D and sucrose liquid medium having a pH effective for culturing said protoplasts which is 4.0 to 4.7 on an agar support.

21. The method of claim 20, wherein said conditioned media contains at least 80% by weight of a medium which has been used for cell culturing.

22. The method of claim 21, wherein cultivation is carried out in the dark for 30 days.

* * * * *

UNITED STATES PATENT AND TRADEMARK OFFICE
CERTIFICATE OF CORRECTION

PATENT NO. : 4,880,744
DATED : Nov. 14, 1989
INVENTOR(S) : Fujimura et al

It is certified that error appears in the above-identified patent and that said Letters Patent is hereby corrected as shown below:

IN THE CLAIMS:

Please amend the following claims.

Claim 3
  Line 1, change "1 or 3" to --1 or 2--.

Claim 4
  Line 1, change "1 or 3" to --1 or 2--.

Claim 6
  Line 1, change "3" to --2--.

Signed and Sealed this

Sixteenth Day of October, 1990

Attest:

HARRY F. MANBECK, JR.

*Attesting Officer*  *Commissioner of Patents and Trademarks*